(12) United States Patent
Goebel

(10) Patent No.: US 10,184,869 B2
(45) Date of Patent: Jan. 22, 2019

(54) APPARATUS AND METHOD FOR MATERIAL TESTING

(71) Applicant: Luvata Franklin, Inc., Franklin, KY (US)

(72) Inventor: Timothy L. Goebel, Woodburn, KY (US)

(73) Assignee: Virtus Precision Tube, LLC, Franklin, KY (US)

( * ) Notice: Subject to any disclaimer, the term of this patent is extended or adjusted under 35 U.S.C. 154(b) by 134 days.

(21) Appl. No.: 15/029,546

(22) PCT Filed: Oct. 15, 2014

(86) PCT No.: PCT/US2014/060785
§ 371 (c)(1),
(2) Date: Apr. 14, 2016

(87) PCT Pub. No.: WO2015/057901
PCT Pub. Date: Apr. 23, 2015

(65) Prior Publication Data
US 2016/0274014 A1    Sep. 22, 2016

Related U.S. Application Data

(60) Provisional application No. 61/891,375, filed on Oct. 15, 2013.

(51) Int. Cl.
*G01N 17/00* (2006.01)
*G01N 7/10* (2006.01)
*G01N 17/04* (2006.01)

(52) U.S. Cl.
CPC ............. *G01N 7/10* (2013.01); *G01N 17/00* (2013.01); *G01N 17/002* (2013.01);
(Continued)

(58) Field of Classification Search
CPC ...... G01N 7/10; G01N 17/002; G01N 17/006; G01N 17/00; G01N 17/04; G01N 17/046
See application file for complete search history.

(56) References Cited

U.S. PATENT DOCUMENTS 2,976,123 A    3/1961    Marsh et al.
3,492,860 A    2/1970    Bailey
(Continued)

FOREIGN PATENT DOCUMENTS

JP    S6061644    4/1985
WO    0233391    4/2002

OTHER PUBLICATIONS

Orzalli, Preliminary Corrosion Studies of Candidate Materials for Supercritical Water Oxidation Reactor System, Calhoun: The NPS Institutional Archive May 1, 1994.

*Primary Examiner* — Blake A Tankersley
(74) *Attorney, Agent, or Firm* — Hodgson Russ LLP

(57) ABSTRACT

A test fixture for testing a flat sample of a material is disclosed. The test fixture having a test vessel for a fluid selected to test the desired properties of the material. The test fixture having a housing with a first end, a second end, and at least one wall extending from the first end to the second end. The housing may have a cylindrical configuration, a parallelpiped configuration, or other geometries. An opening in the housing is provided for receiving the flat test sample such that the assembled housing and the sample form a pressure vessel with an interior chamber.

15 Claims, 4 Drawing Sheets

(52) U.S. Cl.
CPC ........... *G01N 17/006* (2013.01); *G01N 17/04* (2013.01); *G01N 17/046* (2013.01)

(56) References Cited

U.S. PATENT DOCUMENTS

| | | | |
|---|---|---|---|
| 4,044,605 | A | 8/1977 | Brathall |
| 5,034,190 | A | 7/1991 | Economy et al. |
| 5,388,464 | A | 2/1995 | Maddison |
| 5,419,201 | A | 5/1995 | Li et al. |
| 5,571,955 | A | 11/1996 | Beavers et al. |
| 6,463,791 | B1 * | 10/2002 | Berube ............... G01M 3/2884 73/46 |
| 7,034,553 | B2 | 4/2006 | Gilboe |
| 7,387,031 | B1 | 6/2008 | Perrin et al. |
| 7,553,681 | B2 | 6/2009 | Raravikar et al. |
| 7,581,457 | B2 | 9/2009 | Bussu |
| 8,084,267 | B2 | 12/2011 | Gruter et al. |
| 8,375,803 | B2 | 2/2013 | Butterfield |
| 2002/0033042 | A1 | 3/2002 | Brooker et al. |
| 2006/0077379 | A1 | 4/2006 | Frot et al. |
| 2012/0031188 | A1 | 2/2012 | Dahlstrom |

\* cited by examiner

APPARATUS AND METHOD FOR MATERIAL TESTING

FIELD OF THE DISCLOSURE

The disclosure relates to materials testing, and more particularly to testing materials suitable for use in tubes.

BACKGROUND OF THE DISCLOSURE

The development of new materials for use in manufacturing tubes, such as the tubes used in heat exchangers, often involves testing the new materials for their ability to withstand corrosion. One such test is called a formicary corrosion test, whereby a tube sample is sealed at an end and the tube interior is pressurized. The tube exterior is exposed to a corrosive testing fluid, such as, for example, formic acid, until the tube can no longer maintain the interior pressure.

In order to manufacture a sample of a tube for testing, it is necessary to make an amount of a new material sufficient to run through the tube manufacturing process. The quantity of material made typically far exceeds the amount actually tested. A batch of new material, for example, a copper alloy material, can be expensive to manufacture, particularly because most of the material will never be used (i.e., if the testing proves the material unsuitable for use). Accordingly, there is a need for a lower cost testing methodology for new materials for use in manufacturing tubes.

BRIEF SUMMARY OF THE DISCLOSURE

The present disclosure may be embodied as a test fixture for testing a flat sample of a material. The test fixture has a test vessel configured to contain a testing fluid selected to test the desired properties of the material. The test fixture has a housing with a first end, a second end, and at least one wall extending from the first end to the second end. The housing may have a cylindrical configuration. In other embodiments, the housing is configured as an elongate parallelepiped. Other configurations will be apparent to one having skill in the art in light of the present disclosure. The housing further comprises an opening which is configured to receive the flat test sample such that the assembled housing and the sample form a pressure vessel with an interior chamber.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Preliminarily, a known, exemplary method for formicary corrosion testing tubular samples is described in further detail. Tube samples are manufactured from the test material. The tube samples are cleaned and prepared for testing in accordance with ASTM G 1 ("Preparing, Cleaning, and Evaluating Corrosion Test Specimens"). Two tubes of each test material are tested. Wire bale jars (one liter size) are used as the test vessels. A ⅝" diameter hole is cut in the lid of each jar to allow a straight tube length to be placed in the jar. The test vessels are cleaned and then rinsed with deionized ("DI") water. They are air dried in the inverted position. Teflon fittings are used to make the hole airtight. A piece of polyethylene film covered the jar opening to prevent test vapors from contacting rubber gaskets used to create seals between each and its lid. The tube samples are connected to the test hardware (e.g., a pressure gauge, a brass valve, and tubing) with a Swagelok® connector. Each test vessel is labeled to identify the alloy type, tube number, job number, solution concentration, and test start date.

The test solution was 500-ppm formic acid, which is confirmed with ion chromatography. A 100 mL aliquot of test solution is placed in each test vessel. The tube samples are held suspended 2-inches above the test solution. As such, the tube sample is only in contact with the vapor and condensate of the test solution. A clasp on the lid is fastened. Each tube unit is then pressurized with nitrogen to 100 psig. This pressure is maintained until there is through-wall penetration caused by a formicary pit.

A cyclic temperature protocol is followed in order to accelerate formicary corrosion. At night and on weekends the test vessels are kept in an oven at a temperature of 40° C. During each typical 9 hour work day, the oven is turned off, and an oven door is opened to allow the test vessels to cool to room temperature (~20° C.).

The test vessels are checked every weekday morning when the oven was turned off. The gauge pressure is recorded two hours later when they have cooled to room temperature. When there is a significant drop in pressure, the tube is re-pressurized to 100 psig. If the pressure drops quickly, it is tested to determine leak-location (e.g., bubble) by immersion in water. A section of the tube, including the leak location, is prepared according to ASTM E 3 ("Preparation of Metallographic Specimens") to examine the leak. Microphotographs are taken to record the findings.

Figure 1A:
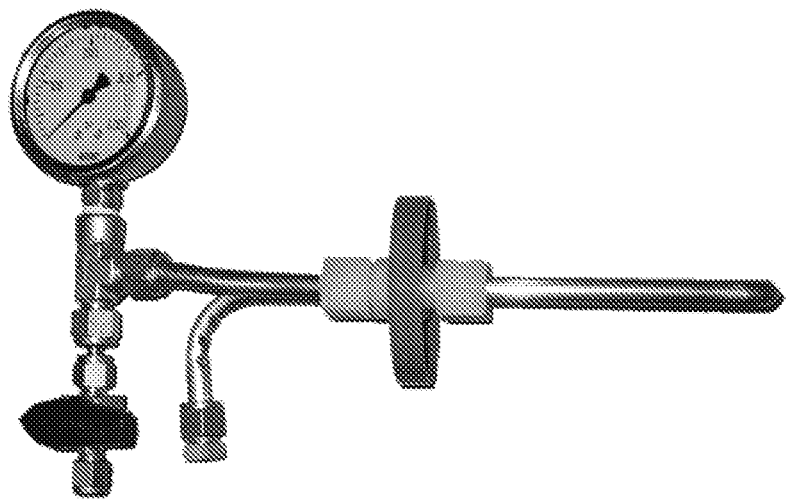
FIG. 1A shows an embodiment of a portion of a prior art test fixture for a tubular sample.
Figure 1B:
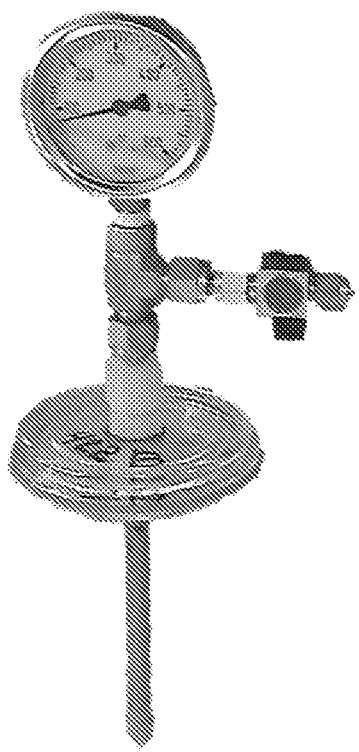
FIG. 1B shows another embodiment of a portion of a prior art test fixture for a tubular sample.
Figure 1C:
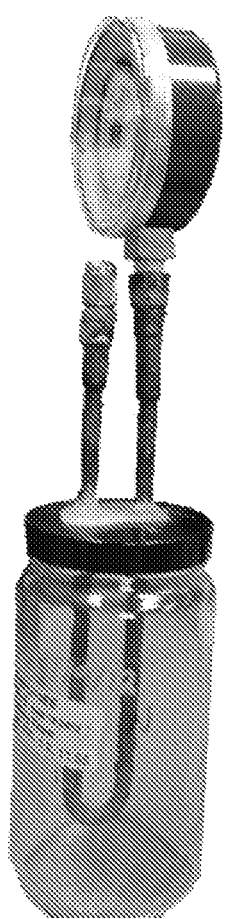
FIG. 1C shows an embodiment of a prior art test fixture for a tubular sample.
Figure 2:
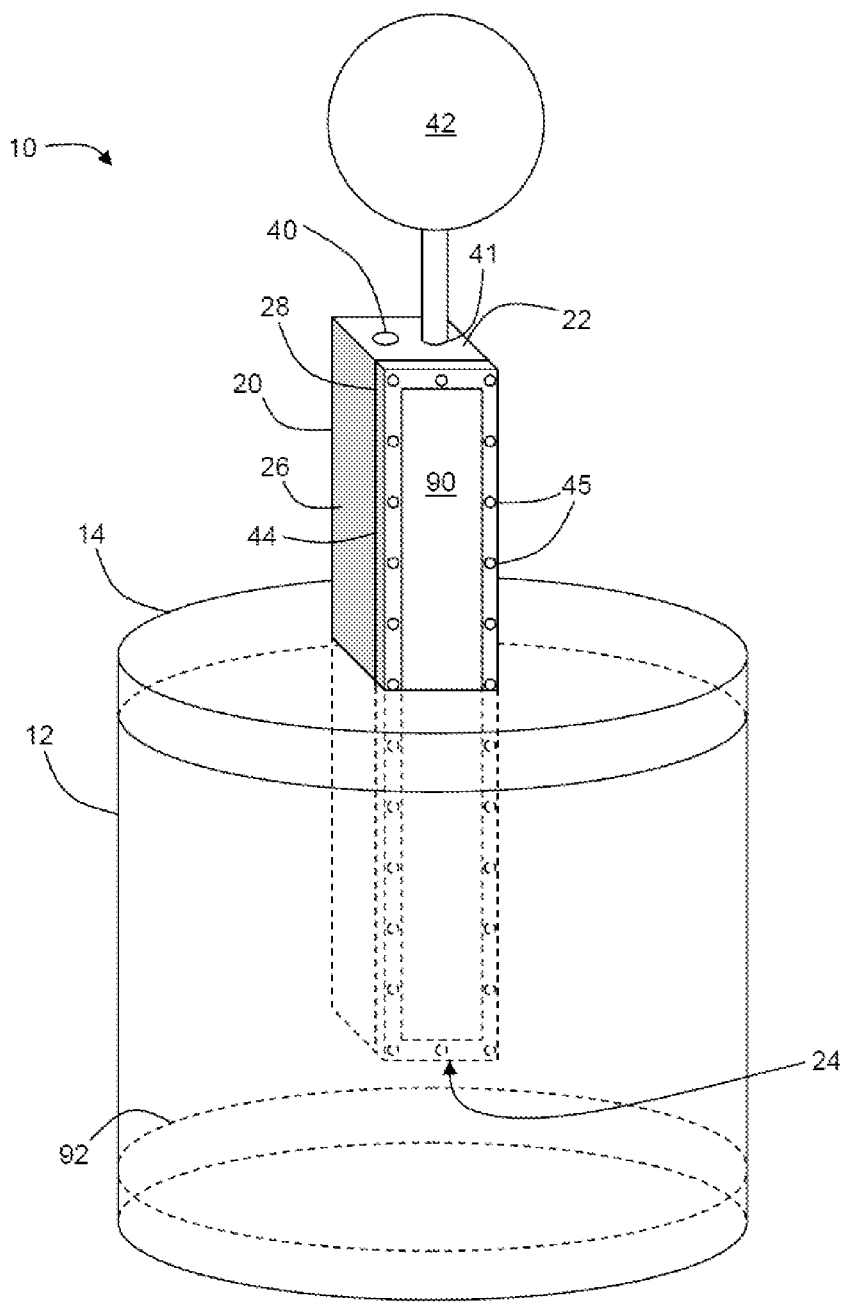
FIG. 2 is a diagram of a test fixture according an embodiment of the present disclosure.

Referring now to FIG. 2, the present disclosure may be embodied as a test fixture 10 for testing a flat sample 90 of a material. The test fixture 10 has a test vessel 12 configured to contain a testing fluid 92. For example, the aforementioned wire bale jar can be used as a test vessel 12. (Although reference is made to a wire bale jar in this disclosure, it should be noted that other embodiments of test vessels 12 are known and are within the scope of the disclosure). The testing fluid 92 may be any testing fluid 92 selected to test the desired properties of the material. For example, the testing fluid 92 may be formic acid and the test vessel 12 is made from a material which is configured to contain the formic acid. Preferably, the material of the test vessel 12 does not react with the testing fluid 92.

Figure 3A:
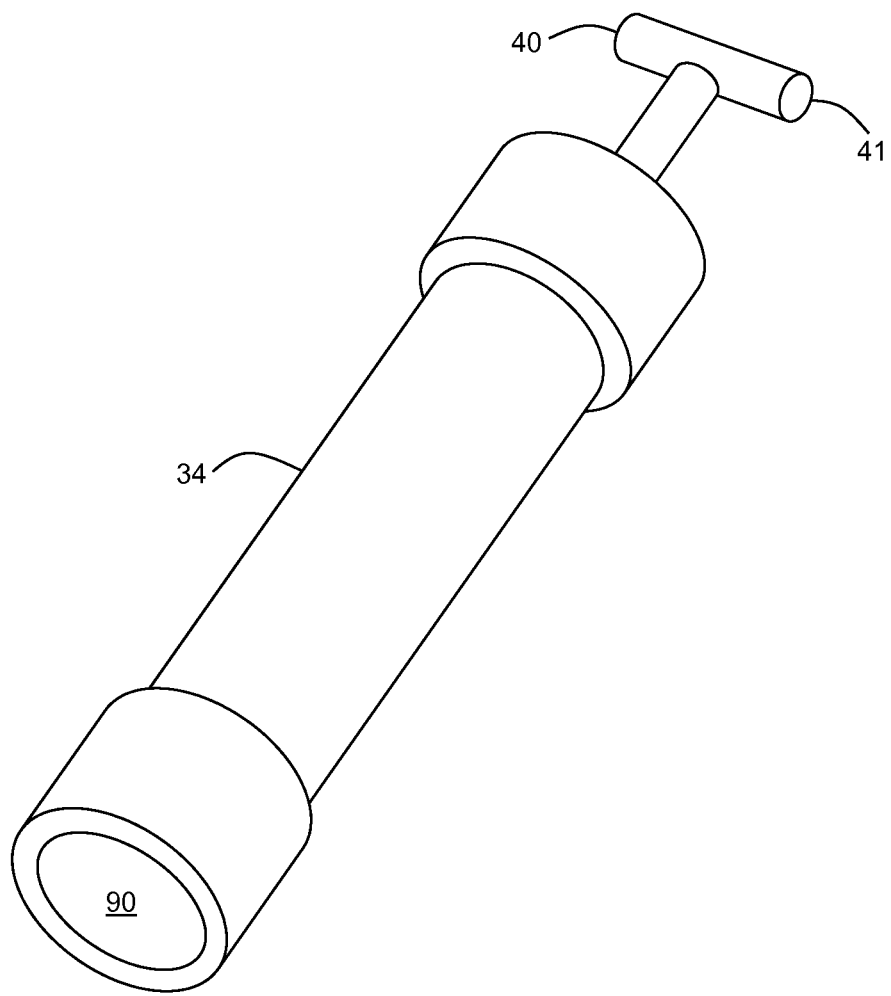
FIG. 3A is a diagram of a portion of a test fixture according to another embodiment of the present disclosure.
Figure 3B:
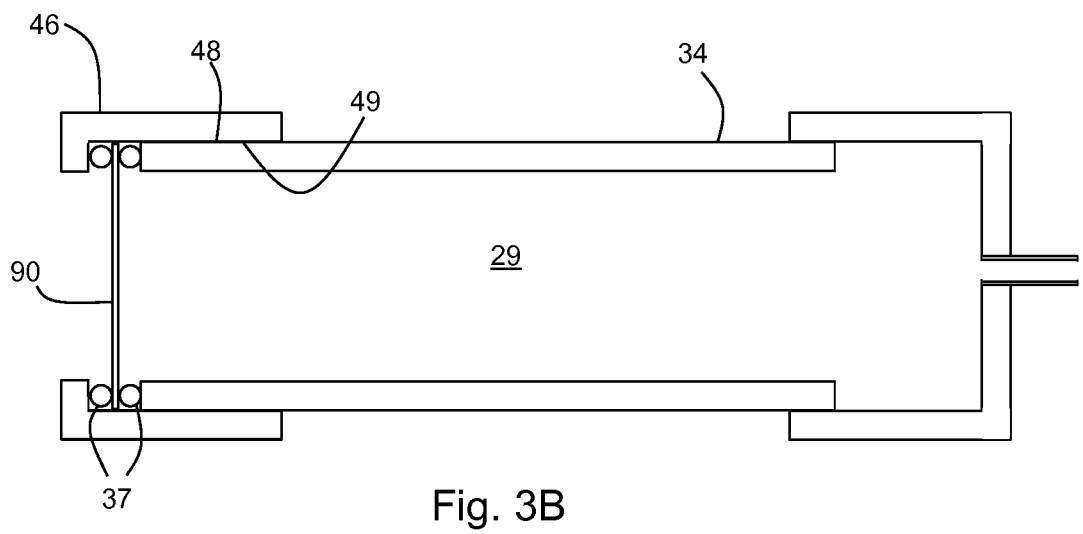
FIG. 3B is a cross-sectional view of the test fixture portion of FIG. 3A.
Figure 4:
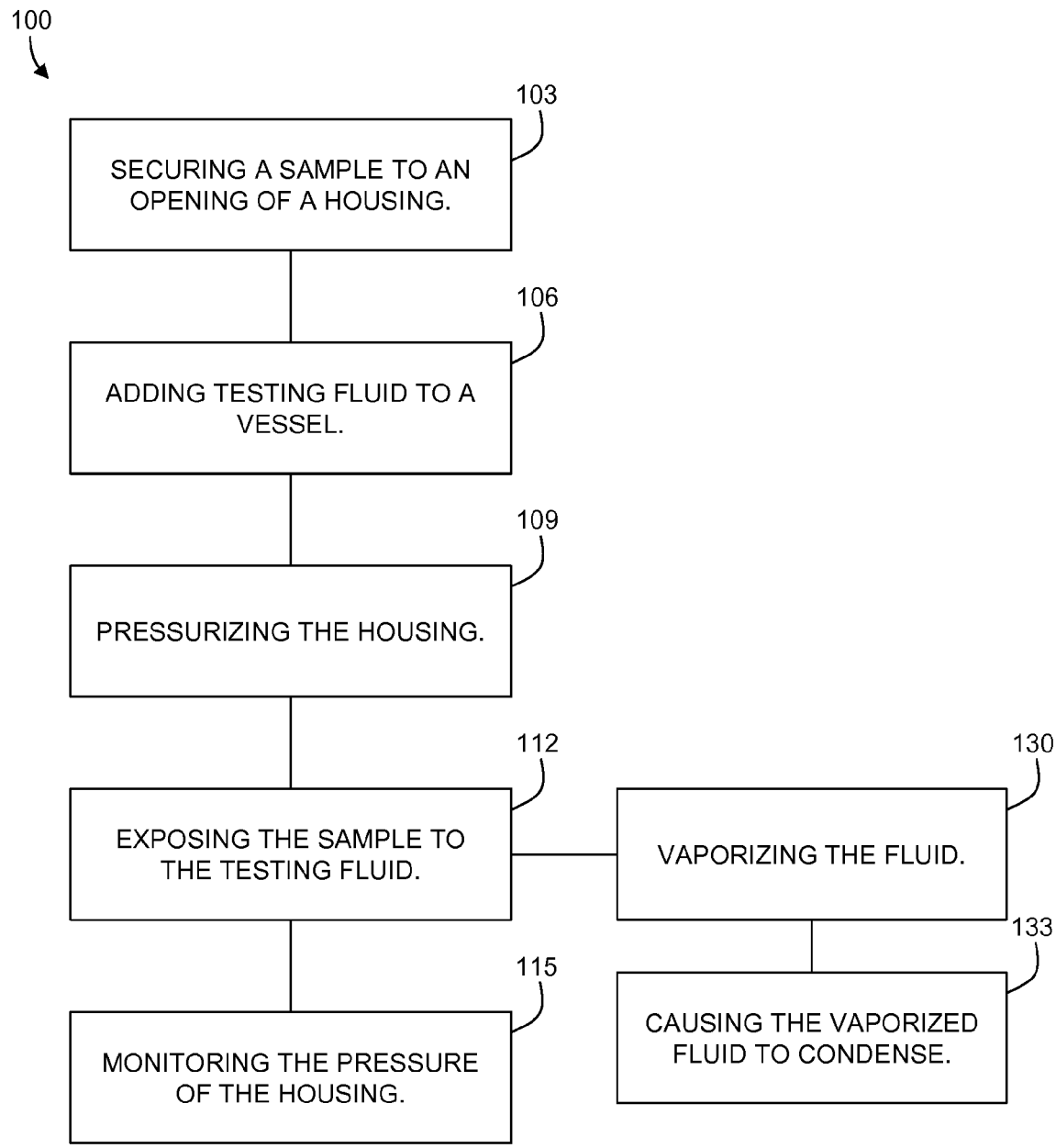
FIG. 4 is a flowchart of a method according to an embodiment of the present disclosure.

The test fixture 10 has a housing 20 with a first end 22 and a second end 24. The housing 20 has at least one wall 26 extending from the first end 22 to the second end 24. In some embodiments, such as the exemplary embodiment depicted in FIG. 3, the housing 40 may have a cylindrical configuration and the cylinder shape is made up of a wall 24. In other embodiments, such as the exemplary embodiment depicted in FIG. 2, the housing 20 is configured as an elongate parallelepiped and the housing 20 may have more the one wall 26.

The housing 20 further comprises an opening 28 which is configured to receive the flat test sample 90. The opening 28 of the housing 20 is configured to sealingly cooperate with the flat shape of the sample 90 such that the assembled housing 20 and the sample 90 form a pressure vessel with an interior chamber 29. The opening 28 may be located in any location on the housing 20, for example, the opening 28 may be located on a wall 26 of the housing. In another example, depicted in FIG. 3, the opening 28 may be located on the first end 32 of the housing 30. The opening 28 may have a seal member 27, such as, for example, an O-ring for providing an air-tight seal with the sample 90 when the sample is attached.

The test fixture 10 may further comprise a retainer 44 for holding the sample 90 on the opening 28 of the housing 20. In the exemplary embodiment depicted in FIG. 2, the retainer 44 is configured as a rectangular ring which is fastened to the housing 20 using a plurality of screws 45, so as to capture the sample 90 between the retainer 44 and the housing 20. In the exemplary embodiment of FIGS. 3A and 3B, the retainer 46 is a circular ring with a lip portion 47 and a threaded portion 48. In this embodiment, the retainer 46 is configured to cooperate with threads 49 on an outer surface of the wall 34 of the housing 30 in order to capture the sample 90 between the retainer 46 and the housing 30. Seal members 37 for providing a fluid-tight seal, are shown in this example. Other retainer configurations will be apparent in light of the present disclosure. Embodiments of the test fixture need not include a retainer 44. For example, a flat sample may be affixed to the housing using an adhesive of sufficient strength. In another example, the sample has a size and shape such that the sample, inserted from the inside of the housing, cannot pass through the opening.

The housing 20 is connected to the test vessel 12 such that at least a portion of the sample 90 is contained by (i.e., within) the test vessel 12. For example, the housing 20 may be elongate and be disposed through a lid 14 of the test vessel 12 such that a portion of the housing 12 is located within the test vessel 12 and a portion is located outside of the test vessel 12. In another embodiment, the housing 20 may be connected to another portion of the test vessel 12, for example a side of the test vessel 12. The housing 20 may be contained entirely within the test vessel 12. Similarly, the housing 20 and test vessel 12 may be configured such that, when a sample is affixed to the housing 20, the sample 90 is disposed through a lid 14 (or other portion) of the test vessel 12 or the sample 90 is located entirely within the test vessel 12 (whether or not the housing 20 is entirely within the test vessel). It should be noted that the housing 20 may be permanently connected to the test vessel 12 or configured for connection to the test vessel 12.

The test fixture 10 has a port 40 in fluid communication with the interior (i.e., interior chamber 29) of the housing 20. The port 40 is configured for connection to a pressurization system such as a source of pressurized gas for pressurizing the housing 20. In another embodiment, the pressurization system to which the port 40 may be connected is configured to reduce the pressure within the housing 20 to a pressure less than ambient (i.e., a vacuum system). The port 40 may be of any configuration, such as, for example, a quick-connect coupling commonly used with pneumatic systems. In some embodiments, the test fixture comprises a pressure gauge 42 in communication with the interior (i.e., interior chamber 29) of the housing 20. For example, the pressure gauge 42 may be connected to the port 40. In another example, the pressure gauge 42 communicates with the interior of the housing via a separate gauge port 41. The pressure gauge 42 is configured to measure a pressure within the housing 20 when the sample 90 is attached and the interior chamber 29 is pressurized or de-pressurized.

It should be noted that embodiments of the housing 20, with or without the test fixture 10, is not limited to use with the above-described formicary corrosion test and can be used with any suitable testing methodology. For example, the housing 20/test fixture 10 may be utilized in a modified salt spray (fog) tests (i.e., ASTM G85). Such tests may be carried out using, for example, acetic acid in a continuous method (ASTM G85 A1), cyclic acidified salt spray (ASTM G85 A2), or any other test(s) where such a device may be useful for testing flat samples.

The present disclosure may be embodied as a method 100 testing a flat sample. The method 100 comprises the step of securing 103 the sample to an opening of a housing to form a pressure chamber. The housing may be, for example, a housing configured as described herein. As such, the sample may be secured 103 to the opening using, for example, a retaining ring or an adhesive. In another example, the sample may be secured 103 by inserting the sample into the housing and against the opening from the inside of the housing. Other securing structures will be apparent in light of the present disclosure.

A testing fluid is placed 106 into a test vessel. The testing fluid is selected to be corrosive to the sample. For example, the testing fluid may be formic acid. Other testing fluids are known and can be used (for example, water, salt water, etc.) The housing is connected 109 to the test vessel such that at least a portion of the test sample is contained within the test vessel. The pressure chamber of the housing is pressurized 109. For example, the housing is connected to a source of pressurized gas (for example, nitrogen, air, etc.) and the pressurized gas is communicated to the interior of the housing. In another example, the housing is pressurized with a liquid. In some embodiments, the pressurization liquid may be different in appearance from the testing fluid. For example, the pressurization liquid may be dyed. It should be noted that pressurizing the housing should be broadly construed to include embodiments where the housing is de-pressurized. In this way, pressurizing can be thought of as causing a differential between a pressure in the interior of the pressure chamber and a pressure outside of the pressure chamber.

At least a portion of the sample is exposed 112 to the testing fluid within the test vessel. For example, as mentioned above in the prior art formicary corrosive test, in embodiments wherein the testing fluid is a liquid, the testing fluid may be heated and at least a portion of the testing fluid is vaporized 130. In this way the sample is exposed 112 to the vaporized 130 testing fluid. The vaporized 130 fluid may be caused to condense 133 on the sample.

The pressure of the pressure chamber of the housing is monitored 115 to determine when the corrosion of the sample caused by exposure to the testing sample compromises the integrity of the pressure chamber.

Although the present disclosure has been described with respect to one or more particular embodiments, it will be understood that other embodiments of the present disclosure may be made without departing from the spirit and scope of the present disclosure.

I claim:

1. An apparatus for testing a flat sample, comprising:
a test vessel configured to contain a testing fluid, wherein the test vessel comprises a lid;
a housing having a first end, a second end, at least one wall, and an opening configured to sealingly receive the sample such that the housing and the sample form a pressure vessel having an interior chamber, and wherein the housing is connected to the test vessel such that at least a portion of the sample is contained by the vessel;
a port in fluid communication with the interior chamber of the housing, the port configured for fluid communication with a pressurization source;
a pressure gauge in communication with the interior chamber of the housing.

2. The apparatus of claim 1, further comprising a retainer for retaining the sample on the opening of the housing.

3. The apparatus of claim 1, further comprising a seal member around the opening of the housing for cooperating with the sample to provide a fluid-tight seal between the housing and the sample.

4. The apparatus of claim 1, wherein the housing is affixed to the lid of the test vessel.

5. The apparatus of claim 1, wherein the housing is configured to be affixed to the lid after the sample is received by the opening of the housing.

6. The apparatus of claim 1, wherein the opening is at the first end of the housing.

7. The apparatus of claim 1, wherein the opening is at a side of the housing.

8. A method for testing a flat sample, comprising the steps of:
securing the sample to an opening of a housing to form a pressure chamber;
placing a testing fluid within a test vessel, the testing fluid selected to be corrosive to the sample;
connecting the housing in the test vessel such that at least a portion of the sample is contained within the test vessel;
pressurizing the pressure chamber of the housing;
exposing at least a portion of the sample to the testing fluid; and
monitoring the pressure of the pressure chamber of the housing to determine when the corrosion of the sample caused by exposure to the testing sample compromises the pressure chamber.

9. The method of claim 8, wherein the pressure chamber is pressurized using nitrogen gas.

10. The method of claim 8, wherein the pressure chamber is pressurized using a liquid.

11. The method of claim 8, wherein the pressure chamber is pressurized to 100 psig.

12. The method of claim 8, wherein the pressure chamber is pressurized by reducing the pressure.

13. The method of claim 8, wherein the testing fluid is formic acid.

14. The method of claim 8, further comprising the steps of:
raising the temperature of the testing fluid to cause at least a portion of the testing fluid to vaporize; and
causing at least a portion of the vaporized testing fluid to condense on the sample.

15. The method of claim 14, wherein the steps of raising the temperature of the testing fluid and causing at least a portion of the vaporized testing fluid to condense on the sample are repeated.

* * * * *